US00PP22953P2

(12) United States Plant Patent
Brown

(10) Patent No.: US PP22,953 P2
(45) Date of Patent: Aug. 14, 2012

(54) ***MANDEVILLA* PLANT NAMED 'SOPHIA'**

(50) Latin Name: *Mandevilla hybrida*
Varietal Denomination: Sophia

(75) Inventor: Graham Noel Brown, Pennant Hills (AU)

(73) Assignees: Floraquest Pty. Ltd., Pennant Hills, NSW (AU); Protected Plant Promotions Australia Pty. Ltd., Macquarie Fields, NSW (AU)

( * ) Notice: Subject to any disclaimer, the term of this patent is extended or adjusted under 35 U.S.C. 154(b) by 60 days.

(21) Appl. No.: 12/927,775

(22) Filed: Nov. 22, 2010

(51) Int. Cl.
*A01H 5/00* (2006.01)

(52) U.S. Cl. ..... Plt./232

(58) Field of Classification Search ..... Plt./232
See application file for complete search history.

*Primary Examiner* — June Hwu
(74) *Attorney, Agent, or Firm* — C. A. Whealy

(57) ABSTRACT

A new and distinct cultivar of *Mandevilla* plant named 'Sophia', characterized by its compact, upright and mounding plant habit; strong stems; early and freely flowering habit; and large bright crimson red-colored flowers.

1 Drawing Sheet

Botanical designation: *Mandevilla hybrida.*
Cultivar denomination: 'SOPHIA'.

CROSS-REFERENCED TO CLOSELY-RELATED APPLICATIONS

Title: *Mandevilla* Plant Named 'Vivian'
Applicant: Graham Noel Brown
Filed: Concurrently with this application (U.S. patent application Ser. No. 12/927,776)

BACKGROUND OF THE INVENTION

The present invention relates to a new and distinct cultivar of *Mandevilla* plant, botanically known as *Mandevilla hybrida* and hereinafter referred to by the name 'Sophia'.

The new *Mandevilla* plant is a product of a planned breeding program conducted by the Inventor in Pennant Hills, New South Wales, Australia. The objective of the breeding program is to create new shrub-type *Mandevilla* plants with strong stems and numerous attractive flowers.

The new *Mandevilla* plant originated from a cross-pollination made by the Inventor in Pennant Hills, New South Wales, Australia in December, 2003, of a proprietary selection of *Mandevilla hybrida* identified as code number X02.5, not patented, as the female, or seed parent with *Mandevilla hybrida* 'Sunmandecrim', disclosed in U.S. Plant Pat. No. 15,539, as the male, or pollen, parent. The new *Mandevilla* plant was discovered and selected by the Inventor as a single flowering plant from within the progeny of the stated cross-pollination in a controlled greenhouse environment in Macquarie Fields, New South Wales, Australia in November, 2005.

Asexual reproduction of the new *Mandevilla* plant by cuttings in Macquarie Fields, New South Wales, Australia, since December, 2005, has shown that the unique features of this new *Mandevilla* plant are stable and reproduced true to type in successive generations.

SUMMARY OF THE INVENTION

Plants of the new *Mandevilla* have not been observed under all possible environmental conditions. The phenotype may vary somewhat with variations in cultural practices and environment such as temperature and light intensity without, however, any variance in genotype.

The following traits have been repeatedly observed and are determined to be the unique characteristics of 'Sophia'. These characteristics in combination distinguish 'Sophia' as a new and distinct *Mandevilla* plant:

1. Compact, upright and mounding plant habit.
2. Strong stems.
3. Early and freely flowering habit.
4. Large bright crimson red-colored flowers.

Plants of the new *Mandevilla* can be compared to plants of the female parent selection. Plants of the new *Mandevilla* differ from plants of the female parent selection in the following characteristics:

1. Plants of the new *Mandevilla* are more upright than and not as vining as plants of the female parent selection.
2. Plants of the new *Mandevilla* flower earlier than plants of the female parent selection.

Plants of the new *Mandevilla* can be compared to plants of the male parent, 'Sunmandecrim'. Plants of the new *Mandevilla* differ from plants of 'Sunmandecrim' in the following characteristics:

1. Plants of the new *Mandevilla* are more compact than plants of 'Sunmandecrim'.
2. Plants of the new *Mandevilla* have thicker stems than plants of 'Sunmandecrim'.

Plants of the new *Mandevilla* can be compared to plants of *Mandevilla hybrida* 'Vivian', disclosed in a U.S. Plant Patent application filed concurrently with this application. Plants of the new *Mandevilla* differ primarily from plants of 'Vivian' in flower color as plants of 'Vivian' have red purple-colored flowers. In addition, plants of the new *Mandevilla* are more compact and have shorter internodes than plants of 'Vivian'.

Plants of the new *Mandevilla* can also be compared to plants of *Mandevilla sanderi* 'Fisrix Dered', disclosed in U.S. Plant Pat. No. 20,714. Plants of the new *Mandevilla* differ primarily from plants of 'Fisrix Dered' in the following characteristics:

1. Plants of the new *Mandevilla* are more compact than plants of 'Fisrix Dered'.

2. Plants of the new *Mandevilla* have thicker stems than plants of 'Fisrix Dered'.
3. Plants of the new *Mandevilla* have larger flowers than plants of 'Fisrix Dered'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the bottom of the sheet comprises a side perspective view of a typical flowering plant of 'Sophia' grown in a container.

The photograph at the top of the sheet is a close-up view of a typical flowering plant of 'Sophia'.

DETAILED BOTANICAL DESCRIPTION

The aforementioned photographs and following observations, measurements and values describe plants grown in one-gallon containers during the summer in a polyethylene-covered greenhouse in Bonsall, Calif. under commercial production cultural practices. During the production of the plants, day temperatures ranged from 20° C. to 29.4° C., night temperatures ranged from 15.6° C. to 21.1° C. and light levels ranged from 5,000 to 8,000 foot-candles. Plants were pinched four times and were six months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Sophia'.

Parentage:

*Female, or seed, parent*.—Proprietary selection of *Mandevilla hybrida* identified as code number X02.5, not patented.

*Male, or pollen, parent*.—*Mandevilla hybrida* 'Sunmandecrim', disclosed in U.S. Plant Pat. No. 15,539.

Propagation:

*Type*.—By cuttings.

*Time to produce a rooted young plant*.—About one month.

*Root description*.—Fleshy, thick; white in color.

*Rooting habit*.—Moderate branching; medium density.

Plant description:

*Plant and growth habit*.—Compact, upright and mounding plant habit; vigorous growth habit.

*Plant height*.—About 30 cm.

*Plant diameter*.—About 32 cm.

*Lateral branch description*.—Branching habit: Freely branching habit with about five primary lateral branches per plant; primary laterals with secondary laterals; pinching enhances lateral branch development. Length: About 19 cm. Diameter: About 3 mm. Internode length: About 1.5 cm to 2.5 cm. Strength: Strong. Texture: Smooth, glabrous; woody with development. Color, young: Close to 144A. Color, woody: Close to 199A.

Foliage description:

*Arrangement*.—Opposite, simple.

*Length*.—About 6.3 cm.

*Width*.—About 4.5 cm.

*Shape*.—Elliptical.

*Apex*.—Acuminate.

*Base*.—Obtuse.

*Margin*.—Entire.

*Texture, upper and lower surfaces*.—Smooth, glabrous; leathery.

*Venation pattern*.—Pinnate, arcuate.

*Color*.—Developing leaves, upper surface: Brighter green than 137A. Developing leaves, lower surface: Close to 146B. Fully expanded leaves, upper surface: Close to N137D; venation, close to 144A. Fully expanded leaves, lower surface: Close to 146B; venation, close to 147C.

*Petioles*.—Length: About 1.3 cm. Diameter: About 2 mm. Texture, upper and lower surfaces: Smooth, glabrous. Color, upper surface: Close to 147C. Color, lower surface: Close to 146D.

Flower description:

*Flower type and habit*.—Salverform flowers arranged in terminal and axillary clusters; flowers face upright or outwardly; freely flowering habit, about three flowers per cluster and about 20 open flowers and flower buds develop per plant.

*Natural flowering season*.—Plants flower continuously year-round in the greenhouse and outdoors in Southern California.

*Flower longevity on the plant*.—About five to seven days; flowers persistent.

*Fragrance*.—None detected.

*Flowers*.—Appearance: Funnelform with five-parted fused corolla; flowers roughly star-shaped. Diameter: About 7 cm. Depth (length): About 7.5 cm. Throat diameter: About 1.6 cm. Tube length: About 6 cm. Tube diameter, at the base: About 5 mm.

*Flower buds*.—Height: About 7.4 cm. Diameter: About 1.4 cm. Shape: Elongated oblong. Color: Towards the apex, close to 183A; mid-section, close to 185A; towards the base, close to 145C.

*Corolla*.—Arrangement/appearance: Single whorl of five petals, fused into flared trumpet; petals imbricate with reflexed apices. Petal lobe length: About 3 cm. Petal lobe width: About 2.8 cm. Petal lobe shape: Roughly ovate, asymmetrical. Petal apex: Acute, reflexing. Petal margin: Entire, slightly sinuate. Petal texture, upper and lower surfaces: Smooth, glabrous; velvety. Throat texture: Smooth, glabrous. Tube texture: Smooth, glabrous. Color: Petal lobe, when opening, upper surface: Slightly brighter than 183B. Petal lobe, when opening, lower surface: Close to 183C. Petal lobe, fully opened, upper surface: Close to 53A; venation, close to 53A. Petal lobe, fully opened, lower surface: Close to 46A; venation, close to 46A. Throat: Close to N172B; venation, close to N172B. Tube: Close to 60B; venation, close to 60D.

*Sepals*.—Arrangement/appearance: Five per flower fused in a single whorl. Calyx length: About 1.3 cm. Calyx diameter: About 5 mm. Shape: Lanceolate. Apex: Acuminate. Margin: Entire. Texture, upper and lower surfaces: Smooth, glabrous. Color, inner surface: Close to 145B to 145C. Color, outer surface: Close to 145B.

*Peduncles*.—Length: About 3.2 cm. Diameter: About 2 mm. Texture: Smooth, glabrous. Strength: Strong, flexible. Aspect: About 45° from stem axis. Color: Close to 145A.

*Pedicels*.—Length: About 1.2 cm to 2.3 cm. Diameter: About 2.5 mm. Texture: Smooth, glabrous. Strength: Strong, flexible. Aspect: About 45° from peduncle axis. Color: Close to 145A.

*Reproductive organs*.—Stamens: Quantity per flower: Typically five. Filament length: About 3 mm. Filament color: Close to 150D. Anther shape: Narrowly oblong. Anther length: About 9 mm Anther color: Close to 18B. Pollen amount: Scarce. Pollen color: Close to 4D. Pistils: Quantity per flower: Typically one. Pistil length: About 2.4 cm. Stigma shape: Rounded; five-lobed. Stigma color: Close to 144A. Style length: About 1.3 cm. Style color: Close to 145C. Ovary color: Close to 146B.

*Seed/fruit*.—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 2° C. to about 35° C.

It is claimed:

1. A new and distinct *Mandevilla* plant named 'Sophia' as illustrated and described.

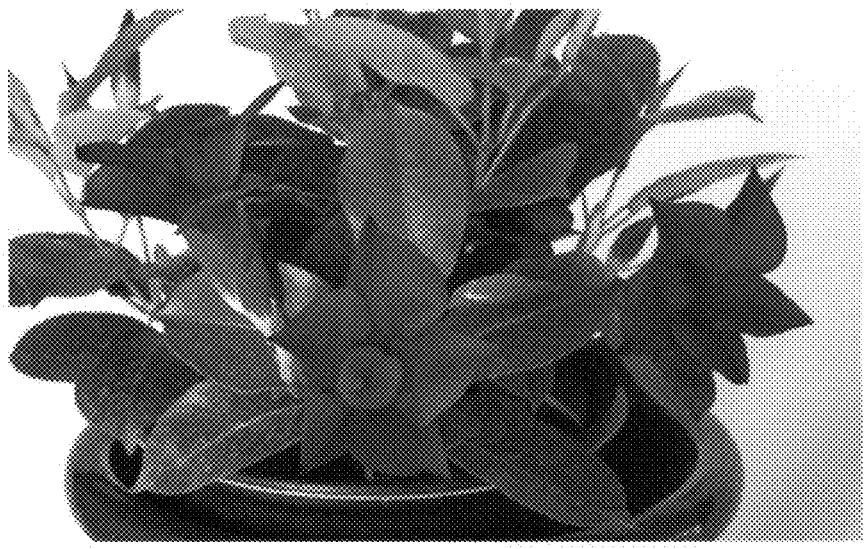
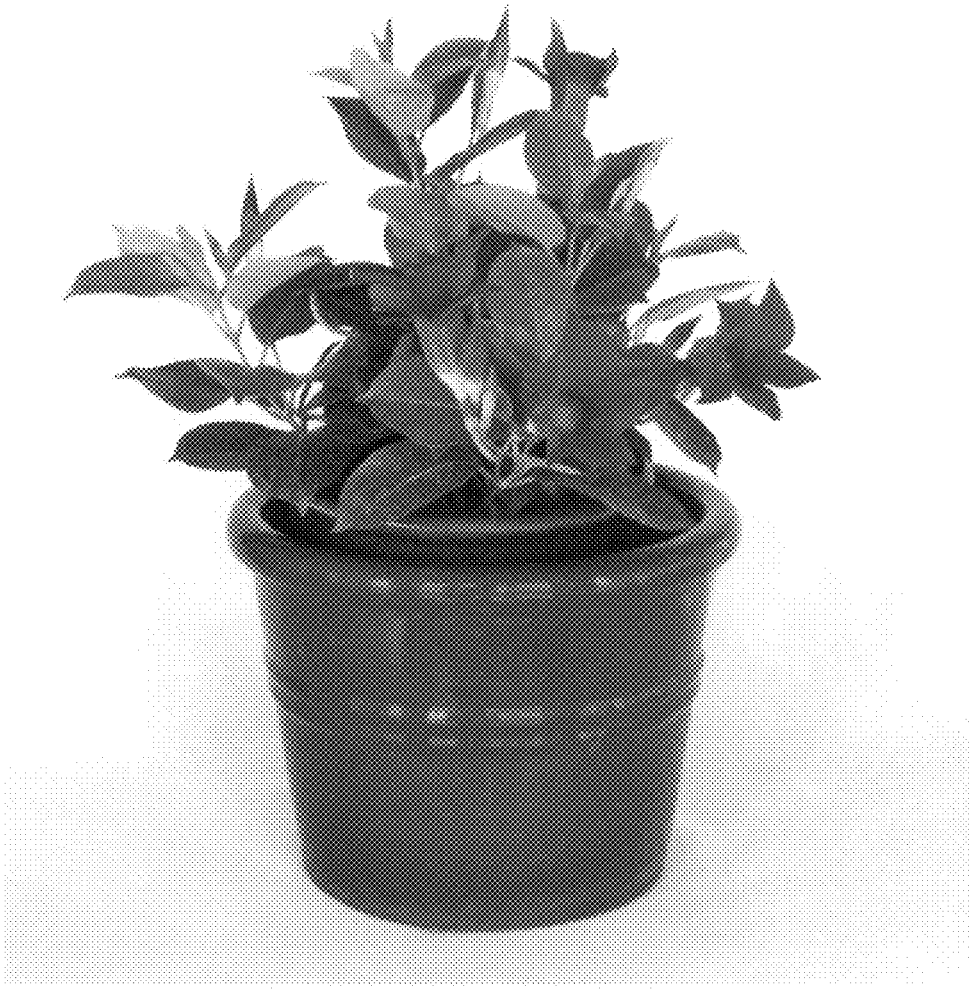

* * * * *